(12) United States Patent
Raslambekov

(10) Patent No.: US 10,342,641 B1
(45) Date of Patent: ***Jul. 9, 2019

(54) SYSTEMS AND METHODS FOR MAKING ORTHODONTIC APPLIANCES

(71) Applicant: 3D MED AG, Zug (CH)

(72) Inventor: Islam Khasanovich Raslambekov, Moscow (RU)

(73) Assignee: 3D MED AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/291,515

(22) Filed: Mar. 4, 2019

Related U.S. Application Data

(63) Continuation of application No. 16/146,316, filed on Sep. 28, 2018, now Pat. No. 10,278,794.

(51) Int. Cl.
*G06F 19/00* (2018.01)
*A61C 7/28* (2006.01)
*A61C 13/00* (2006.01)
*A61C 7/00* (2006.01)
*B22F 3/105* (2006.01)
*B33Y 80/00* (2015.01)

(52) U.S. Cl.
CPC .............. *A61C 7/28* (2013.01); *A61C 7/002* (2013.01); *A61C 13/0018* (2013.01); *A61C 13/0019* (2013.01); *B22F 3/1055* (2013.01); *B33Y 80/00* (2014.12)

(58) Field of Classification Search
CPC ....... A61C 7/28; A61C 7/002; A61C 13/0018; A61C 13/0019; B33Y 80/00; B22F 3/1055
See application file for complete search history.

(56) References Cited

U.S. PATENT DOCUMENTS

| 6,193,923 | B1* | 2/2001 | Leyden .................. B29C 41/12 264/308 |
|---|---|---|---|
| 8,057,226 | B2 | 11/2011 | Wiechmann et al. |
| 8,694,142 | B2 | 4/2014 | Yang et al. |
| 2006/0093992 | A1 | 5/2006 | Wen |
| 2007/0178423 | A1 | 8/2007 | Rubbert et al. |

(Continued)

FOREIGN PATENT DOCUMENTS

DE      102016112499 A1      1/2018

OTHER PUBLICATIONS

U.S. Appl. No. 16/146,316, filed Sep. 28, 2018.

*Primary Examiner* — Michael D Masinick
(74) *Attorney, Agent, or Firm* — BCF LLP

(57) ABSTRACT

A method for making an orthodontic appliance comprising: receiving, by a processor of a computer system, a three-dimensional digital model of an orthodontic appliance; determining, by the processor, a compensation factor to be applied when manufacturing the orthodontic appliance using the laser-based system, the determining the compensation factor including: aligning the three-dimensional digital model of the orthodontic appliance in a three-dimensional space with a predetermined position; determining a deviation of a position of a model groove base from a desired position of the model groove base, the compensation factor being based on the deviation and relating to an amount of material to be used during the manufacturing of the orthodontic appliance; causing the laser-based system to apply the compensation factor for manufacturing the orthodontic appliance.

18 Claims, 9 Drawing Sheets

(56) References Cited

U.S. PATENT DOCUMENTS

| | | |
|---|---|---|
| 2008/0141534 A1 | 6/2008 | Hilliard et al. |
| 2010/0316972 A1 | 12/2010 | Klare et al. |
| 2010/0324715 A1 | 12/2010 | Yang et al. |
| 2012/0285019 A1 | 11/2012 | Schechner et al. |
| 2015/0164618 A1 | 6/2015 | Heacock et al. |
| 2016/0175072 A1 | 6/2016 | Andreiko et al. |
| 2016/0199154 A1 | 7/2016 | Schlimper et al. |
| 2016/0302884 A1 | 10/2016 | Paehl et al. |
| 2017/0049534 A1 | 2/2017 | Soo et al. |
| 2017/0245962 A1 | 8/2017 | Skamser et al. |

* cited by examiner

SYSTEMS AND METHODS FOR MAKING ORTHODONTIC APPLIANCES

CROSS-REFERENCE

The present application is a continuation of U.S. patent application Ser. No. 16/146,316, filed Sep. 28, 2018, the entirety of which is incorporated herein by reference.

FIELD

The present technology relates to systems and methods for making orthodontic appliances.

BACKGROUND

In orthodontics, treatments for achieving alignment of malposed teeth in a patient include applying orthodontic appliances to the patient's teeth or to the patient's oral cavity. One type of orthodontic appliance comprises dental braces. Dental braces typically have two components: orthodontic brackets which are attached to the teeth via a bracket rear face in a rear portion of the bracket, and an orthodontic archwire receivable in a groove formed in a front portion of the bracket. In use, a plurality of teeth of a patient's archform each has a bracket attached thereto, with the archwire received in the respective groove of each of the brackets and extending across the brackets. Archwires are typically made from shape memory alloys which have the ability to recover their shape when heated. The archwire is pre-shaped and attached to the brackets by bending its shape to conform to the general shape of the malposed teeth. When the archwire warms to mouth temperature it reverts to its original shape thereby exerting a force on the teeth to which it is attached to move them.

A number of factors affect the actual force applied to the teeth by the dental braces, and the resultant orthodontic effect. One of these factors is the fit between the bracket groove and the archwire. A good fit is achieved when the full diameter of the archwire is received fully in the bracket groove with minimal relative movement between these two brace components.

However, one or both of the bracket groove and the archwire may deviate in size or shape, resulting in an imperfect fit between the bracket and the archwire. This can lead to a deviation of the expected force to be applied by the dental braces and an unexpected orthodontic effect.

During planning of an orthodontic treatment, dental practitioners may select specific combinations of archwire diameter, archwire material and bracket groove size for a specific orthodontic effect. For example, a stiffer archwire material can exert a higher force than a less stiff material, and a thicker archwire can exert a higher force than a thinner archwire. These selections are made based on predicted forces assuming a correct fit between the archwire and the brackets. Therefore, an imperfect fit between the archwire and the bracket will result in unexpected and unplanned orthodontic effect.

An unexpected orthodontic effect can prolong a patient's treatment duration and extend the pain, inconvenience and expense of orthodontic treatment. It can also cause more serious damage, such as bone resorption and tooth loss.

It is an object of the present technology to ameliorate at least some of the inconveniences present in the prior art.

SUMMARY

Embodiments of the present technology have been developed based on developers' appreciation of certain shortcomings associated with the existing systems for determining an orthodontic treatment.

Developers have observed that the size and configuration deviations contributing to an imperfect fit between a bracket and an archwire include one or more of: the relative angle between the bracket groove wall and the bracket groove base deviating from a desired angle, the relative angle between the bracket groove walls deviating from a desired angle, rounded corners within the groove, and surface asperities or defects in the walls or base of the groove.

Developers have also noted that certain manufacturing practices are more prone to producing brackets with these deviations. For example, casting of metal alloy brackets is a known technique in the art for making brackets, but has a number of drawbacks.

One drawback is that depending on the metal alloy being cast, an oxide film can form on the surface of the cast metal. The oxide film adds an additional thickness, which cannot be easily predicted meaning that compensation for the additional thickness during the casting process is not possible. The oxide film is also problematic for the rear surface of the bracket as deviations from the exact contour of the tooth can mean an inadequate adhesion to the tooth to which it is being attached.

Another drawback of the casting method is that it is difficult to reproducibly make fine structural elements of the bracket, e.g. the bracket groove, and any patterns on the rear side to help with adhesion to the tooth. This is because during metal alloy casting, linear shrinkage of the molten metal occurs meaning that there is a thickness limit of the structure that can be cast.

Three-dimensional laser-based additive manufacturing has been considered as an alternative for making orthodontic brackets (see for example, US 2010/0324715). Manufacturing using laser-based systems is a potentially economical method for making custom-made orthodontic appliances as individual bracket molds are not required as for casting methods. Items can be made, layer by layer, according to a three-dimensional digital model of the item. However, these additive manufacturing methods have not been perfected for orthodontic brackets and therefore give rise to inaccuracies with the structures that are made.

In particular, Developers have noted difficulties in achieving accurate sizes and configurations of different parts of the bracket groove or the bracket rear surface when manufacturing the orthodontic bracket using a laser-based system. One such laser-based system used is a selective laser sinter system. Specifically, Developers have noted that the angle of orientation of the bracket being manufactured relative to the incident laser beam path is an important factor in being able to achieve a target dimension. For a given spot size of incident laser beam in the laser-based system, a deviation from the intended dimension of the bracket being manufactured is noted when the incident laser beam angle is more or less than 90 degrees relative to the surface being manufactured. For example, Developers have noted a deviation of the laser beam path of up to 30 microns.

Therefore, it is difficult to achieve a target dimension in the different parts of the orthodontic bracket being manufactured which have a different angle from one another relative to the incident laser beam path. Although a support can be provided to build the orthodontic bracket at an optimal angle relative to the laser beam path for one part of the orthodontic bracket (e.g. the rear surface), another component of the orthodontic bracket with a different angle relative to the laser beam path will have a diminished structural accuracy (e.g. the bracket groove).

Furthermore, although finishing techniques exist for orthodontic brackets which compensate for deviations of size and configuration of the bracket groove after their manufacture (see for example, US 2016/0302884, and DE102016112499), a two-step procedure is not ideal and adds to the time and cost of manufacture of each bracket.

Additionally, the Developers of the present technology have determined advantageous material properties of the orthodontic bracket, when the orthodontic bracket, or at least the groove base of the orthodontic bracket, is manufactured by the laser-based system in a single operation.

Accordingly, from a broad aspect, the present technology provides a laser-based system for manufacturing an orthodontic bracket with precise dimensions. More specifically, the present technology provides orthodontic brackets with precise bracket groove dimensions as well as bracket rear surface dimensions. The bracket rear surface can be manufactured to conform to a patient's tooth contour.

According to certain broad aspects of the present technology, a compensation factor is determined for being applied during the manufacturing of at least a certain a portion of the orthodontic bracket to correct for angle-related deviations of the laser-beam. In certain embodiments, this enables the manufacture of the orthodontic bracket with dimensions matching target dimensions.

From one aspect, there is provided a method for making an orthodontic appliance having a body defining a groove, the groove having a first groove side wall, a second groove side wall opposing the first groove side wall, and a groove base separating the first and second groove side walls, the method executable by a processor of a computer system operatively connected to a laser-based system, the method comprising: receiving, by the processor, a three-dimensional digital model of the orthodontic appliance, the three-dimensional digital model having a model body defining a model groove, the model groove having a model groove first side wall, a model groove second side wall opposing the model groove first side wall, and a model groove base separating the first and second groove model side walls; determining, by the processor, a compensation factor to be applied when manufacturing the orthodontic appliance using the laser-based system, the determining the compensation factor including: aligning the three-dimensional digital model of the orthodontic appliance in a three-dimensional space with a predetermined position; determining a deviation of a position of the model groove base from a desired position of the model groove base, the compensation factor being based on the deviation and relating to an amount of material to be used during the manufacturing of the orthodontic appliance; and causing the laser-based system to apply the compensation factor for manufacturing the orthodontic appliance.

From another aspect, there is provided a method for making an orthodontic bracket having a body defining a groove for receiving at least a portion of an archwire in use, the groove having a first groove side wall, a second groove side wall opposing the first groove side wall, and a groove base separating the first and second groove side walls, the method executable by a processor of a computer system operatively connected to a laser-based system, the method comprising: receiving, by the processor, a three-dimensional digital model of the orthodontic bracket, the three-dimensional digital model having a model body defining a model groove, the model groove having a model groove first side wall, a model groove second side wall opposing the model groove first side wall, and a model groove base separating the first and second groove model side walls; determining, by the processor, a compensation factor to be applied when manufacturing the orthodontic bracket using the laser-based system, the determining the compensation factor including: aligning the three-dimensional digital model of the orthodontic bracket in a three-dimensional space with a predetermined position; determining a deviation of a position of the model groove base from a desired position of the model groove base, the compensation factor being based on the deviation and relating to an amount of material to be used during the manufacturing of the orthodontic bracket; causing the laser-based system to apply the compensation factor for manufacturing the orthodontic bracket.

In certain embodiments, the amount of material to be used is the amount of the material to be used to define the groove base. In certain embodiments, the amount of material is for reducing the material applied when defining the groove base. In certain embodiments, the amount of material to be used is the amount of material required to manufacture the bracket with a desired dimension of the groove. In certain embodiments, the amount of material to be used is the amount of material required to manufacture the appliance with a desired dimension of the groove.

In certain embodiments, the desired position is a reference plane substantially perpendicular to the path of the laser beam of the laser-based system, and the position of the model groove base is a plane of the model groove base. The compensation factor may be based on an angle of deviation between the plane of the model groove base and the reference plane.

In certain embodiments, determining the compensation factor comprises accessing a pre-determined table of compensation factors. The compensation factor may comprise a decrease in material used to form the groove base of the orthodontic device proportional to a decrease in the groove size based on a deviation of the groove base.

In certain embodiments, the three-dimensional digital model further includes an indication of a target manufactured dimension of the groove, and wherein the compensation factor is instrumental in causing the groove, once manufactured, to meet the target manufactured dimension of the groove. In certain embodiments, the amount of material to be used is the amount of material required to manufacture the bracket with the target manufactured dimension of the groove. In certain embodiments, the amount of material to be used is the amount of material required to manufacture the appliance with the target manufactured dimension of the groove.

In certain embodiments, the compensation factor is a parameter that changes a dimension of the groove that will be sent as an instruction to the laser-based system, and which results in the actual manufactured bracket/appliance having a groove matching the target manufactured dimension of the groove.

In certain embodiments, the target manufactured dimension of the groove is one or more of: a substantially 90 degree angle between the first groove side wall and the groove base; a substantially 90 degree angle between the second groove side wall and the groove base; and the first groove side wall and the second groove side wall being substantially parallel.

In certain embodiments, the predetermined position of the three-dimensional digital model of the orthodontic appliance/bracket comprises a predetermined x, y position of the model groove base of the three-dimensional model. In certain embodiments, the predetermined position of the three-dimensional digital model of the orthodontic appliance/bracket does not include taking into account a z-direction position of the model groove base of the three-dimensional digital model.

In certain embodiments, the aligning the three-dimensional digital model comprises identifying the model groove from the three-dimensional digital model, determining if the model groove base is aligned with the predetermined x, y position, and if the model groove base is not aligned with the predetermined x, y position, causing the three-dimensional digital model of the orthodontic appliance/bracket to move in the three-dimensional space to the predetermined x, y position.

In certain embodiments, the method further comprises causing the laser-based system to manufacture at least one of (i) the groove base of the orthodontic appliance/bracket, and (ii) the orthodontic appliance/bracket in a single operation.

In certain embodiments, the method further comprises causing the laser-based system to manufacture the orthodontic bracket based on model bracket dimensions adapted by the compensation factor to achieve the target manufactured dimension of the groove. In certain embodiments, the method further comprises causing the laser-based system to manufacture the orthodontic appliance based on model bracket dimensions adapted by the compensation factor to achieve the target manufactured dimension of the groove.

In certain embodiments, the method further comprises causing the laser beam to move stochastically when manufacturing the orthodontic appliance/bracket. In certain embodiments, the laser-based system is a selective laser sinter system.

In certain embodiments, the method further comprises obtaining tooth data on a tooth of a patient, and generating the three-dimensional digital model of the orthodontic bracket using at least a portion of the tooth data. In certain embodiments, the method further comprises obtaining tooth data on a tooth of a patient, and generating the three-dimensional digital model of the orthodontic appliance/bracket using at least a portion of the tooth data.

In certain embodiments, the method further comprises receiving, by the processor, the three-dimensional digital model of the orthodontic appliance/bracket and importing the three-dimensional digital model into a three-dimensional space. In certain embodiments, the method comprises determining a position for a support for the appliance/bracket during manufacturing. In certain embodiments, determining the position for the support comprises identifying at least one critical zone of the orthodontic appliance, the critical zone being at least a portion of the orthodontic appliance/bracket which will not come into contact with the support during manufacturing of the orthodontic appliance/bracket. In certain embodiments, the critical zone is predetermined. In certain embodiments, the critical zone is one or more of the model groove and the model rear surface.

From a further aspect, there is provided a system for making an orthodontic appliance having a body defining a groove, the groove having a first groove side wall, a second groove side wall opposing the first groove side wall, and a groove base separating the first and second groove side walls, the system comprising: a computer system, operatively connected to a laser-based system, and having a processor arranged to determine a compensation factor to be applied when manufacturing the orthodontic appliance using the laser-based system, and a laser-based system for manufacturing the orthodontic appliance based on instructions from the processor of the computer system, including the compensation factor. In certain embodiments, the laser-based system is a selective laser sintering system.

From another aspect, there is provided a system for making an orthodontic bracket having a body defining a groove for receiving at least a portion of an archwire in use, the groove having a first groove side wall, a second groove side wall opposing the first groove side wall, and a groove base separating the first and second groove side walls, the system comprising: a computer system, operatively connected to a laser-based system, and having a processor arranged to determine a compensation factor to be applied when manufacturing the orthodontic bracket using the laser-based system, and a laser-based system for manufacturing the orthodontic device based on instructions from the processor of the computer system, including the compensation factor. In certain embodiments, the laser-based system is a selective laser sintering system.

In certain embodiments, the processor is arranged to: receive a three-dimensional digital model of the orthodontic appliance/bracket, the three-dimensional digital model having a model body defining a model groove, the model groove having a model groove first side wall, a model groove second side wall opposing the model groove first side wall, and a model groove base separating the first and second groove model side walls; determine the compensation factor by: aligning the three-dimensional digital model of the orthodontic appliance/bracket in a three-dimensional space with a predetermined position; and determining a deviation of a position of the model groove base from a desired position of the model groove base, the compensation factor being based on the deviation and relating to an amount of material to be used during the manufacturing of the orthodontic appliance/bracket.

In certain embodiments, the processor of the system is arranged to perform the method steps as described above.

From a yet further aspect, there is provided a method for making an orthodontic bracket having a front portion defining a groove for receiving at least a portion of an archwire in use, and a rear portion having a rear surface for bonding to a surface of a tooth of a patient, the method executable by a processor of a computer system operatively connected to a laser-based system, the method comprising: receiving, by the processor, a three-dimensional digital model of the orthodontic bracket; determining, by the processor, a compensation factor to be applied to the movement of a laser beam of the laser-based system when manufacturing at least one of the front portion or the rear portion of the bracket, wherein the compensation factor relates to an amount of material to be used during the manufacturing of the orthodontic bracket when manufacturing at least one of the front portion or the rear portion of the bracket at an angle relative to the incident laser beam which is not an optimized angle for laser-based manufacturing; and causing the laser-based system to manufacture the orthodontic bracket based on the three-dimensional digital model and the compensation factor during manufacturing of at least one of the front portion or the rear portion of the orthodontic bracket.

From a further aspect, there is provided a method for making an orthodontic appliance having a first portion defining a groove, and a second portion having a rear surface, the method executable by a processor of a computer system operatively connected to a laser-based system, the method comprising: receiving, by the processor, a three-dimensional digital model of the orthodontic appliance; determining, by the processor, a compensation factor to be applied to the movement of a laser beam of the laser-based system when manufacturing at least one of the first portion or the second portion of the appliance, wherein the compensation factor relates to an amount of material to be used during the manufacturing of the orthodontic appliance when manufacturing at least one of the first portion or second portion of the appliance at an angle relative to the incident laser beam which is not an optimized angle for laser-based manufacturing; and causing the laser-based system to manufacture the orthodontic appliance based on the three-dimensional digital model and the compensation factor during manufacturing of at least one of the first portion or the second portion of the orthodontic bracket.

In certain embodiments, the determining the compensation factor comprises: aligning the three-dimensional digital model of the orthodontic appliance/bracket in a three-dimensional space with a predetermined position; determining a deviation of a position of a model groove base of the three-dimensional digital model from a desired position of the model groove base, the compensation factor being based on the deviation of the position and relating to an amount of material to be used during the manufacturing of the orthodontic appliance/bracket.

From a yet further aspect, there is provided a system for making an orthodontic bracket having a front portion defining a groove for receiving at least a portion of an archwire in use, and a rear portion having a rear surface for bonding to a surface of a tooth of a patient, the system comprising a computer system operatively connected to a laser-based system, and having a processor arranged to determine a compensation factor to be applied when manufacturing the orthodontic bracket using the laser-based system, wherein the processor is arranged to: receive a three-dimensional digital model of the orthodontic bracket; and determine the compensation factor to be applied to the movement of a laser beam of the laser-based system when manufacturing at least one of the front portion or the rear portion of the bracket, wherein the compensation factor relates to an amount of material to be used during the manufacturing of the orthodontic bracket when manufacturing at least one of the front portion or the rear portion of the bracket at an angle relative to the incident laser beam which is not an optimized angle for laser-based manufacturing; and causing the laser-based system to manufacture the orthodontic bracket based on the three-dimensional digital model and the compensation factor during manufacturing of at least one of the front portion or the rear portion of the orthodontic bracket.

From a yet further aspect, there is provided a system for making an orthodontic bracket having a front portion defining a groove for receiving at least a portion of an archwire in use, and a rear portion having a rear surface for bonding to a surface of a tooth of a patient, the system comprising a computer system operatively connected to a laser-based system, and having a processor arranged to determine a compensation factor to be applied when manufacturing the orthodontic bracket using the laser-based system, wherein the processor is arranged to: receive a three-dimensional digital model of the orthodontic bracket; and determine the compensation factor to be applied to the movement of a laser beam of the laser-based system when manufacturing at least one of the front portion or the rear portion of the bracket, wherein the compensation factor relates to an amount of material to be used during the manufacturing of the orthodontic bracket when manufacturing at least one of the front portion or the rear portion of the bracket at an angle relative to the incident laser beam which is not an optimized angle for laser-based manufacturing; and causing the laser-based system to manufacture the orthodontic bracket based on the three-dimensional digital model and the compensation factor during manufacturing of at least one of the front portion or the rear portion of the orthodontic bracket.

From another aspect, there is provided a system for making an orthodontic appliance having a first portion defining a groove, and a second portion having a rear surface, the system comprising a computer system operatively connected to a laser-based system, and having a processor arranged to determine a compensation factor to be applied when manufacturing the orthodontic appliance using the laser-based system, wherein the processor is arranged to: receive a three-dimensional digital model of the orthodontic appliance; and determine the compensation factor to be applied to the movement of a laser beam of the laser-based system when manufacturing at least one of the first portion or the second portion of the appliance, wherein the compensation factor relates to an amount of material to be used during the manufacturing of the orthodontic appliance when manufacturing at least one of the first portion or the second portion of the appliance at an angle relative to the incident laser beam which is not an optimized angle for laser-based manufacturing; and causing the laser-based system to manufacture the orthodontic appliance based on the three-dimensional digital model and the compensation factor during manufacturing of at least one of the first portion or the second portion of the orthodontic appliance.

In certain embodiments, the processor of the system is arranged to align the three-dimensional digital model of the orthodontic appliance/bracket in a three-dimensional space with a predetermined position; and determine a deviation of a position of a model groove base of the three-dimensional digital model from a desired position of the model groove base, the compensation factor being based on the deviation of the position and relating to an amount of material to be used during the manufacturing of the orthodontic appliance/bracket.

In certain embodiments, the processor of the system is arranged to perform the method steps as described above.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Implementations of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

It should be noted that, unless otherwise explicitly specified herein, the drawings are not to scale.

DETAILED DESCRIPTION

Certain aspects and embodiments of the present technology, are directed to systems and methods for making an orthodontic appliance. Broadly, certain aspects and embodiments of the present technology comprise systems and methods for making an orthodontic appliance which minimizes, reduces or avoids the problems noted with the prior art. Notably, certain embodiments of the present technology provide orthodontic appliances with more precise dimensions and configurations. In certain embodiments, the manufacturing tolerances may be reduced and the chances of surface irregularities reduced or minimized.

In certain embodiments, the orthodontic appliance comprises an orthodontic bracket 10 to which aspects and embodiments of the present technology can be applied.

Figure 1:
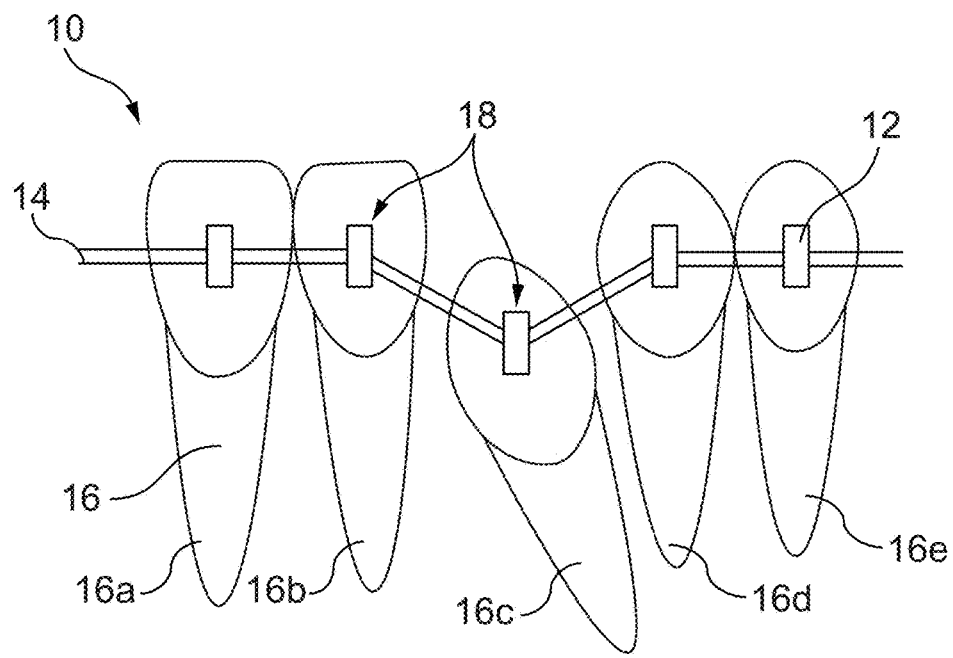
FIG. 1 is a schematic illustration of an orthodontic appliance, comprising brackets and an archwire, applied to five teeth of a plurality of teeth of a patient.
Figures 2, 3:
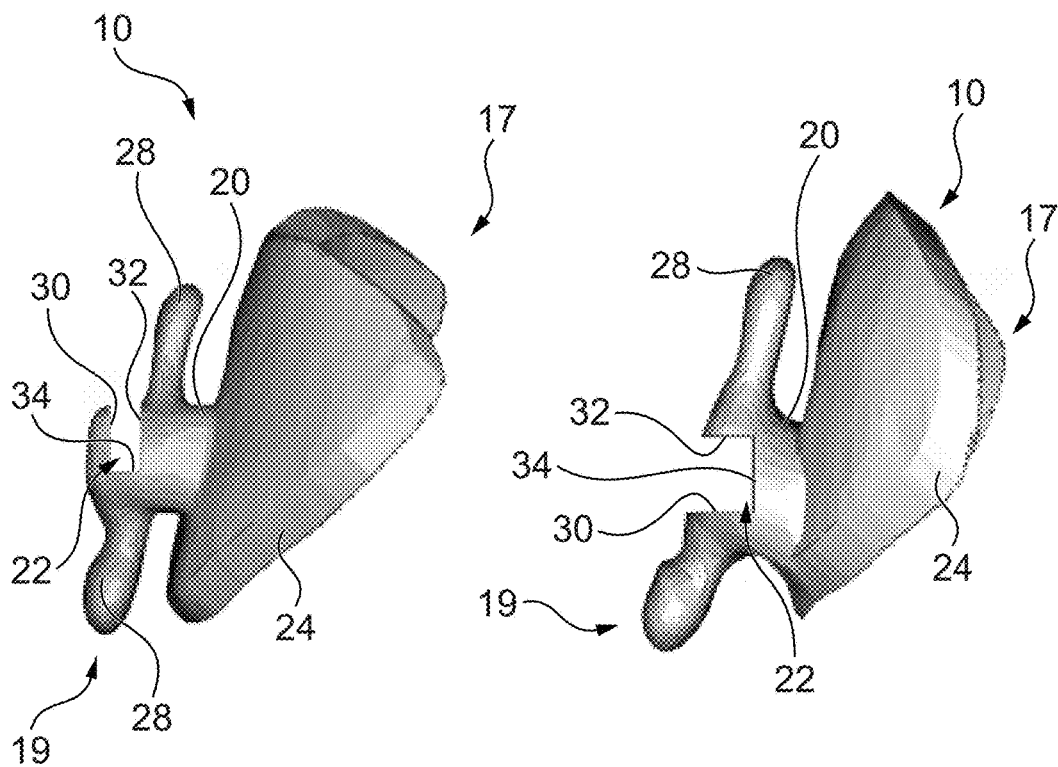
FIG. 2 is a side view of a bracket having a vertical groove, according to certain embodiments of the present technology.
FIG. 3 is a side view of a bracket having a horizontal groove, according to certain embodiments of the present technology.

Referring to FIG. 1, orthodontic brackets 10 (also referred to herein as "brackets 10") are one component of an orthodontic brace system 12 for treating oral malocclusions, the orthodontic brace system comprising a set of brackets 10 interconnected by an archwire 14, each bracket 10 arranged to be bonded to a tooth 16 of a plurality of teeth (e.g. 16a, 16b, 16c, 16d, 16e) of either the lower or upper archform, and to be connected to the archwire 14. The archwire 14 extends between, and is connected to, each of the brackets 10. As illustrated, the maloclusion is misalignment of the tooth 16c for which an upward movement is required to align the tooth 16c with neighbouring the teeth 16a, 16b, 16d, 16e. The archwire 14 is made of a shape memory alloy, in this embodiment Nitinol™, and has a rectangular cross-sectional shape in this embodiment. The archwire 14 has bends 18 which will gradually move towards a pre-shaped position when installed in a mouth of patient due to the shape memory effect of the archwire 14. This will apply a force on the tooth 16c to move it upwardly.

In certain other embodiments, the archwire 14 may be made of any other shape memory alloy or material, for example, nickel-titanium, beta-titanium, cobalt-chromium-nickel, austenitic stainless steel, precious metal alloys (e.g. gold, silver, platinum alloys), polymers (e.g. nylon with silicon dioxide core and silicon resin middle layer, polyphenylene, methacrylate), or be polymer-coated. In certain other embodiments, the archwire 14 has a cross-sectional shape which can be round, square, multi-stranded, triangular, or a super-cable, for example. Various sizes of archwire are currently available including those with rectangular or circular cross-section shapes and having diameters/widths of 0.018 inch, 0.019 inch, 0.020 inch.

As seen in FIGS. 2 to 5, each bracket 10 generally has a rear portion 17 arranged to attach to the tooth 16 and a front portion 19 arranged to attach to the archwire 14. More specifically, the front portion 19 comprises a body 20 defining a groove 22 therein for receiving the archwire 14 in use, and the rear portion 17 comprises a tooth bonding pad 24 extending from the body 20 and having a rear surface 26 for bonding to a surface of the tooth 16. Adhesive is typically used for the bonding (attachment) of the bracket 10 to the tooth 16. In certain embodiments, wings 28 extend from the body 20 on either side of the groove 22, for receiving ties (not shown), such as elastic ties, to secure the archwire 14 in place in the groove 22, in use.

The groove 22, also known as a slot 22, has opposed groove side walls 30, 32 and a groove base 34. A distance between the groove side walls 30, 32 is typically sized to receive a cross-sectional dimension of the archwire 14. In this embodiment, the cross-sectional dimension of the archwire 14 is a width of the archwire 14. For circular cross-section archwires 14, the cross-sectional dimension of the groove 22 is a diameter of the archwire 14. Some of the conventional groove sizes in commercially available brackets are: 0.018" side wall height×0.03" distance between side walls, 0.022" side wall height×0.03" distance between side walls.

As mentioned above, the relative size of the archwire 14 and the bracket groove 22 has been shown to affect the torque applied by the combined bracket-archwire orthodontic appliance. This can be a consideration in choosing particular bracket and archwire size combinations for a desired orthodontic treatment.

The orientation of the groove 22 in the bracket 10 depends on the tooth 16 and the archform to which it is being attached. The bracket 10 of FIG. 2 has a vertical groove 22, and the bracket 10 of FIG. 3 has a horizontal groove 22. In certain other embodiments (not shown), the bracket 10 has a twin configuration comprising two bodies 20 with wings 28, instead of a single configuration of the body 20 with one set of wings 28 shown in FIGS. 2 to 5.

Figure 4:
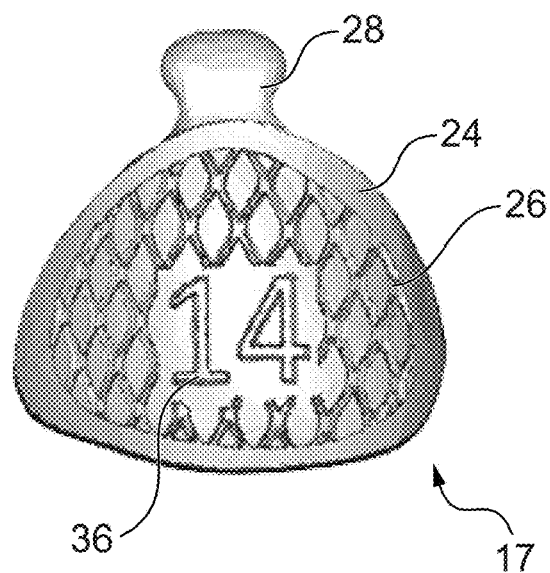
FIG. 4 is a rear side view of the bracket of FIG. 3.

In certain embodiments, the rear surface 26 of the tooth bonding pad 24 of the bracket 10 is textured to increase surface area and to improve adherence to the tooth 16 (FIG. 4). The rear surface 26 of the bracket 10 may also be provided with a label 36, such as a number 36, to indicate the number of the tooth 16 to which it will be applied. This is particularly relevant in the case of brackets 10 which are custom-made. In the embodiment of FIG. 4, the rear surface 26 includes an embossed trellis pattern, and the number "14" to identify the tooth 16 that it is intended to be applied to. In certain embodiments, particularly those embodiments where the brackets are custom-made per patient, a contour of the rear surface 26 corresponds to a contour of the tooth 16 to which it is being applied.

Each bracket 10 is made from a cobalt-chromium alloy. In certain other embodiments, the bracket 10 is made from another metal alloy such as stainless steel or titanium alloy, or a ceramic or a polymer.

It will be appreciated that the brackets 10 can be used with any type of archwire 14 such as those with circular or square cross-sectional profiles, multi-strand wires, etc. Furthermore, the bends 18 in the archwire 14 may comprise rounded corners, loops, or any other appropriate form. It will also be appreciated that the bracket 10 may be used for treating any type of teeth misalignment or malocclusion, including but not limited to closing gaps ("space closure"), creating/widening gaps, tooth rotation, tooth intrusion/extrusion, and translation, to name a few.

Known factors which may affect the force applied by the orthodontic brace system 12 include: the archwire 14 material type and related material properties (e.g. strength, stiffness and elasticity), archwire 14 shape memory properties, and diameter of the archwire 14. Generally, archwires 14 with a broader diameter exert a higher force than narrower archwires 14.

Figure 5A:
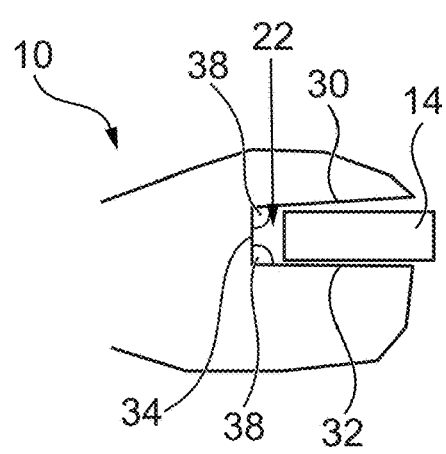
FIGS. 5A, 5B, 5C, and 5D are schematic illustrations of different fits between bracket and archwire pairs of the prior art.
Figure 5B:
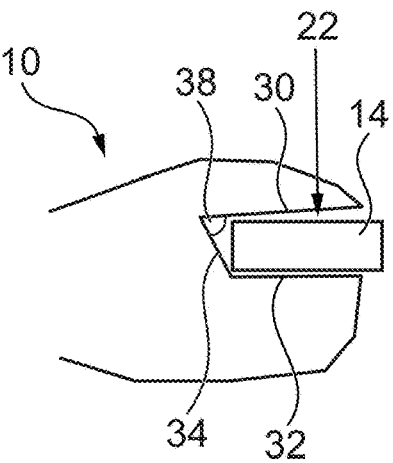
Figure 5C:
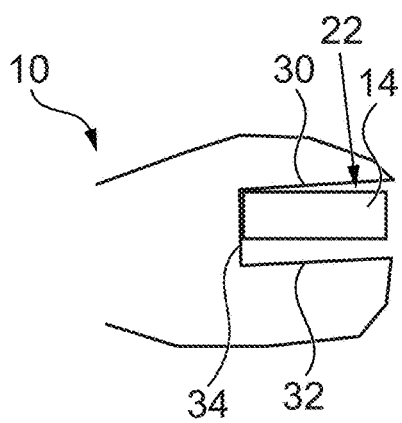
Figure 5D:
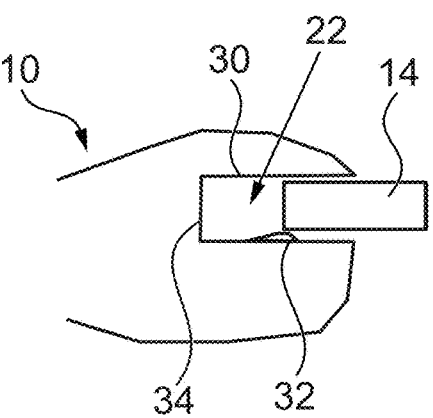

Factors which affect the applied forces in less predictable manner include manufacturing tolerances that affect the fit between the archwire 14 and the bracket 10. An under-sizing of the bracket groove 22 can occur when the distance between the side walls 30, 32 are narrower than expected, or when an angle 38 between any of the side walls 30, 32 and the groove base 34 are more or less than 90 degrees (FIGS. 5A and 5B) which will mean that the archwire 14 is not fully received in the bracket groove 22. An over-sizing of the bracket groove 22 (FIG. 5C) will mean that there is movement of the archwire 14 within the groove 22. Burrs or other surface asperities 40 can also affect the fit (FIG. 5D).

Certain aspects and embodiments of the present technology provide systems 100 and methods 400 for making the brackets 10 with more precise, and reproducible configuration, more specifically, precise groove 22 dimensions and/or precise rear surface 26 dimensions (also referred to herein as "target manufactured dimensions"). In this respect, brackets 10 made by certain aspects and embodiments of the present system 100 and method 400 comprise brackets with the groove side walls 30, 32 and the groove base 34 having dimensions more closely matching target manufactured dimensions. In some embodiments, the groove side walls 30, 32 are substantially parallel to one another, and are substantially perpendicular to the groove base 34.

Figure 6:
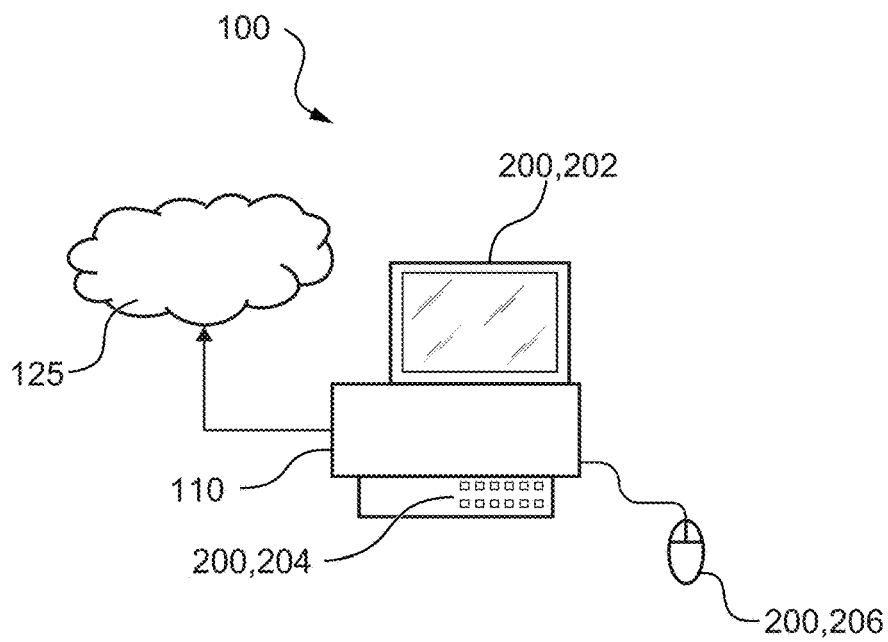
FIG. 6 is a system for making orthodontic brackets, according to certain embodiments of the present technology.

Accordingly, one embodiment of a system 100, suitable for implementing non-limiting aspects and embodiments of the present technology, is shown in FIG. 6. From a broad perspective, the system 100 is arranged to make brackets 10 which closely match a target three-dimensional digital model of the desired bracket, and thereby minimizing or avoiding the chances of an over-fit or an under-fit with the associated archwire 14. In certain embodiments, this is broadly achieved by determining a compensation factor for manufacturing errors and applying the compensation factor during manufacturing.

It is to be expressly understood that the system 100 as depicted is merely an illustrative implementation of the present technology. Thus, the description thereof that follows is intended to be only a description of illustrative examples of the present technology. This description is not intended to define the scope or set forth the bounds of the present technology. In some cases, what are believed to be helpful examples of modifications to the system 100 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 100 may provide in certain instances simple implementations of the present technology, and that where such is the case they have been presented in this manner as an aid to understanding. As persons skilled in the art would understand, various implementations of the present technology may be of a greater complexity.

The system 100 of FIG. 6 comprises a computer system 110 operatively coupled to a laser-based system 120 for making the orthodontic bracket 10. The computer system 110 is arranged to send instructions to the laser-based system 120, according to aspects and embodiments of the method 400 for manufacturing the orthodontic bracket 10.

In certain embodiments, the computer system 110 is connectable to the laser-based system 120 via a communication network 125. In some embodiments, the communication network 125 is the Internet and/or an Intranet. Multiple embodiments of the communication network may be envisioned and will become apparent to the person skilled in the art of the present technology.

Figure 7:
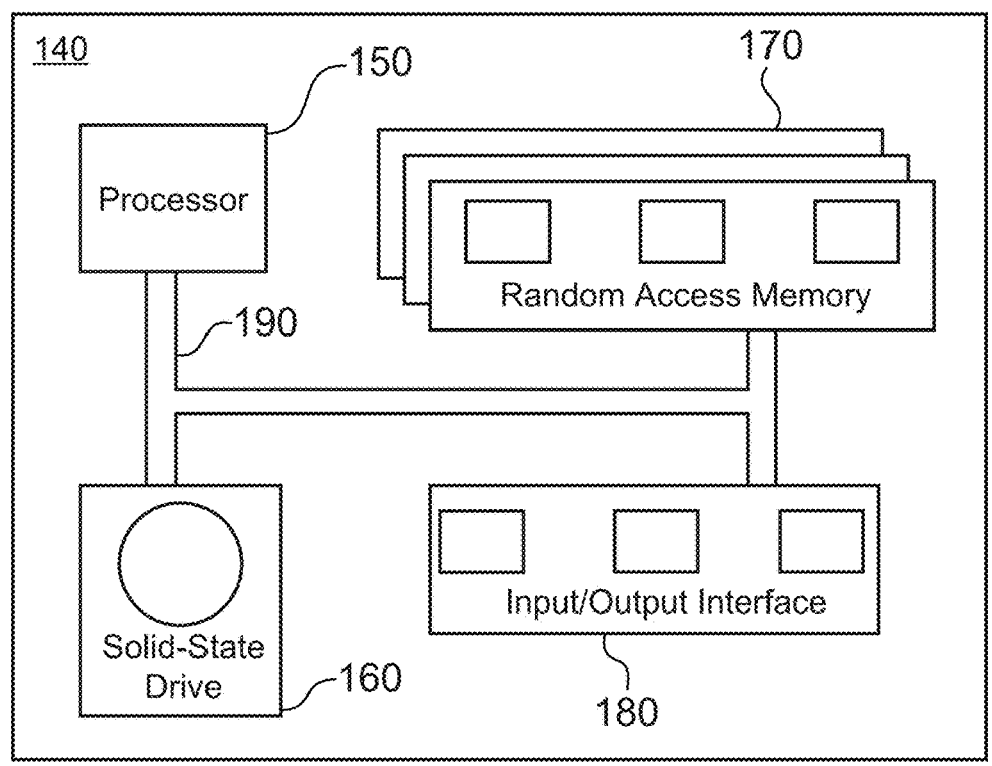
FIG. 7 a computing environment of the system of FIG. 6, according to certain embodiments of the present technology.
Figure 8:
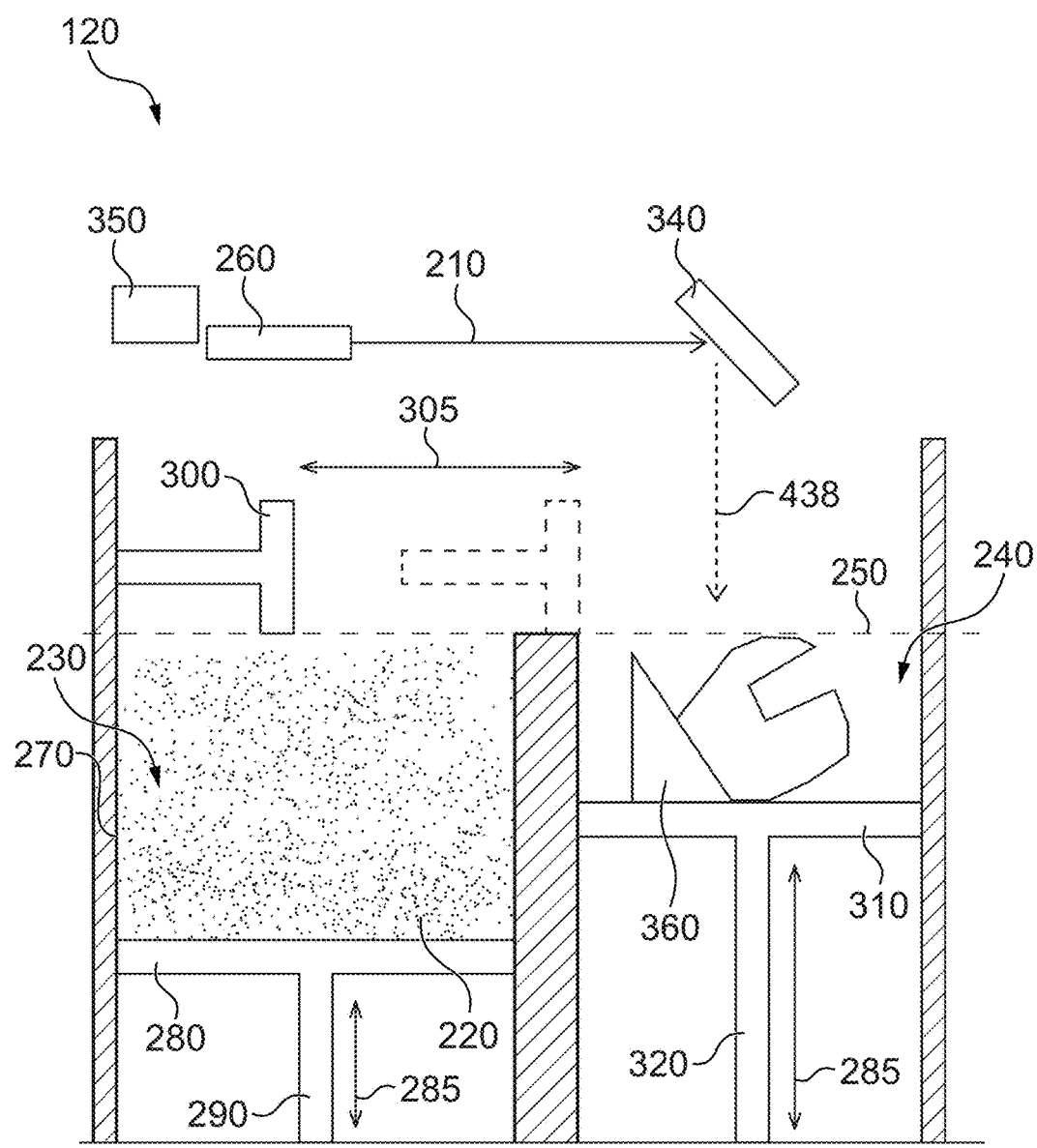
FIG. 8 is a laser-based system for making the orthodontic bracket according to certain embodiments of the present technology.

Turning now to FIG. 7, certain embodiments of the computer system 110 have a computing environment 140 as illustrated schematically in FIG. 8. The computing environment 140 comprises various hardware components including one or more single or multi-core processors collectively represented by a processor 150, a solid-state drive 160, a random access memory 170 and an input/output interface 180. Communication between the various components of the computing environment 140 may be enabled by one or more internal and/or external buses 190 (e.g. a PCI bus, universal serial bus, IEEE 1394 "Firewire" bus, SCSI bus, Serial-ATA bus, ARINC bus, etc.), to which the various hardware components are electronically coupled.

The input/output interface 180 allows enabling networking capabilities such as wire or wireless access. As an example, the input/output interface 180 comprises a networking interface such as, but not limited to, a network port, a network socket, a network interface controller and the like. Multiple examples of how the networking interface may be implemented will become apparent to the person skilled in the art of the present technology. For example, but without being limiting, the networking interface 180 may implement specific physical layer and data link layer standard such as Ethernet™, Fibre Channel, Wi-Fi™ or Token Ring. The specific physical layer and the data link layer may provide a base for a full network protocol stack, allowing communication among small groups of computers on the same local area network (LAN) and large-scale network communications through routable protocols, such as Internet Protocol (IP).

According to implementations of the present technology, the solid-state drive 160 stores program instructions suitable for being loaded into the random access memory 170 and executed by the processor 150 for executing methods 400 according to certain aspects and embodiments of the present technology. For example, the program instructions may be part of a library or an application.

In this embodiment, the computing environment 140 is implemented in a generic computer system which is a conventional computer (i.e. an "off the shelf" generic computer system). The generic computer system is a desktop computer/personal computer, but may also be any other type of electronic device such as, but not limited to, a laptop, a mobile device, a smart phone, a tablet device, or a server.

In other embodiments, the computing environment 140 is implemented in a device specifically dedicated to the implementation of the present technology. For example, the computing environment 140 is implemented in an electronic device such as, but not limited to, a desktop computer/personal computer, a laptop, a mobile device, a smart phone, a tablet device, a server, specifically designed for making the orthodontic bracket. The electronic device may also be dedicated to operating other devices, such as the laser-based system.

In some alternative embodiments, the computer system 110 or the computing environment 140 is implemented, at least partially, on the laser-based system. In some alternative embodiments, the computer system 110 may be hosted, at least partially, on a server. In some alternative embodiments, the computer system 110 may be partially or totally virtualized through a cloud architecture.

Referring back to FIG. 6, the computer system 110 has at least one interface device 200 for providing an input or an output to a user of the system 100, the interface device 200 being in communication with the input/output interface 180. In the embodiment of FIG. 5, the interface device is a screen 202. In other embodiments, the interface device 200 may be a monitor, a speaker, a printer or any other device for providing an output in any form such as image-form, written form, printed form, verbal form, 3D model form, or the like.

In the embodiment of FIG. 7, the interface device 200 also comprises a keyboard 204 and a mouse 206 for receiving input from the user of the system 100. Other interface devices 200 for providing an input to the computer system 110 can include, without limitation, a USB port, a microphone, a camera or the like.

The computer system 110 may be connected to other users, such as through their respective clinics, through a server (not depicted). The computer system 110 may also be connected to stock management or client software which could be updated with stock when orthodontic brackets 10 are ready and/or schedule appointments or follow-ups with clients based on the orthodontic brackets 10 having been prepared.

In some embodiments, the computing environment 140 is distributed amongst multiple systems, such as the laser-based system 120 and/or the server. In some embodiments, the computing environment 140 may be at least partially implemented in another system, as a sub-system for example. In some embodiments, the computer system 110 and the computing environment 140 may be geographically distributed.

As persons skilled in the art of the present technology may appreciate, multiple variations as to how the computing environment 140 is implemented may be envisioned without departing from the scope of the present technology.

Turning now to FIG. 8 which shows one embodiment of the laser-based system 120.

The laser-based system 120 is an additive manufacturing layer technology which uses a high energy beam 210, for example a laser beam 210, to fuse together particles 220 of metal, ceramic, glass or polymeric materials, layer-by-layer into a three-dimensional form. By fusing is meant melting or sintering at least a surface of the particles 220. In certain embodiments of the present technology, the laser-based system 120 is a selective laser sintering system which is arranged to make the bracket 10.

The laser-based system 120 comprises a powder delivery portion 230 for storing and providing the powder 220 to be fused to a fusing portion 240 along a working plane 250. A laser 260 provides the high energy beam 210 which fuses the powder 220 in the fusing portion 240. The fusing can be by any means such as melting or sintering. The powder delivery portion 230 comprises a powder receptacle 270 with a moveable base 280 which can move vertically 285, such as by a piston 290, to provide the powder 220 to a pusher 300. Generally, the moveable base 280 moves gradually upwardly during the manufacturing process to provide powder 220 to the pusher 300 as the powder 220 is depleted in the powder receptacle 270. The pusher 300 is configured to move laterally 305 along the working plane 250 and across an open face of the powder receptacle 270 to engage the powder 220 and provide it to the fusing portion 240.

In the fusing portion 240, there is provided a manufacturing stand 310 onto which the product will be built by fusing the powder 220 using the laser beam 210 according to a predetermined cross-sectional pattern. The manufacturing stand 310 receives the powder 220 from the powder delivery portion 230, which is then fused by the laser beam 210. The manufacturing stand 310 is moveable vertically, such as by a piston 320. Generally, the manufacturing stand 310 is arranged to move downwardly after the production of a layer of the product.

The laser-based system 120 comprises the laser 260 for producing the high energy beam 210, and a mirror unit 340 which is moveable to focus and direct the high energy beam 210 onto the powder 220 at the fusing portion 240. The laser beam 210 has at least one high energy beam path from the mirror unit 340 to the fusing portion 240. In certain embodiments, the laser 260 is a fiber laser with a power of 100 mW, and a spot size of 200 microns. The laser 260 may be a pulsed-type laser. The mirror unit 340 positions the laser beam 210 according to a pre-defined pattern as per the desired horizontal cross-section of the product being made.

The pre-defined pattern is based on a 3D description of the product being made, such as a three-dimensional digital model of the bracket 10, which is sliced to provide the horizontal slice description of the bracket 10. Any suitable software can be used for "slicing" the three-dimensional digital model into layers, such as, but not limited to Magics™ by Materialise™ and "Cambridge™" by 3Shape™.

The three-dimensional digital model can be any format of digital file such as of a type compatible with Computer Aided Design (CAD) software. The pre-defined pattern can also be of any appropriate format, such as OBJ or STL format files.

A processor 350 of the laser-based system 120 controls the movement of the mirror unit 340, as well as the movement of the moveable base 280 of the powder delivery portion 230 and the manufacturing stand 310 of the fusing portion 240. The processor 350 can also receive instructions from the computer system 110 regarding the control of the components of the laser-based device.

In certain embodiments, the powder 220 is a cobalt chromium alloy powder with an average diameter of about 40 microns and a range of about 25-50 microns. When fused, the thickness of each layer is about 15-500 µm, more preferably about 25 microns (equivalent to about 0.025 mm).

The fusing portion 240 can be enclosed to create a sealed chamber for providing an inert environment in the sealed chamber. In order to provide the inert atmosphere, after sealing the chamber of the fusing portion 240, air and humidity is removed from the chamber and the chamber filled with nitrogen.

Figure 9:
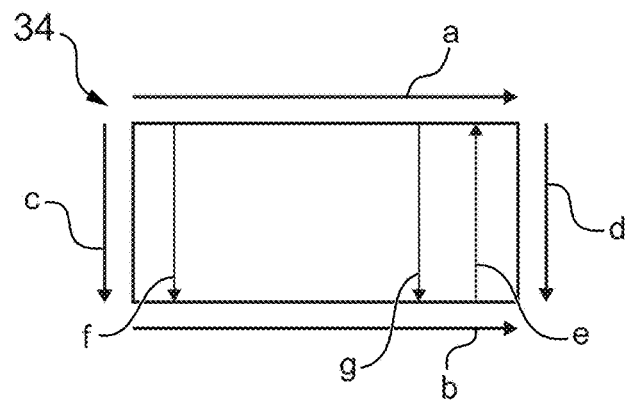
FIG. 9 is a schematic illustration of a stochastic path of movement of a laser beam of the laser-based system of FIG. 9.
Figure 10:
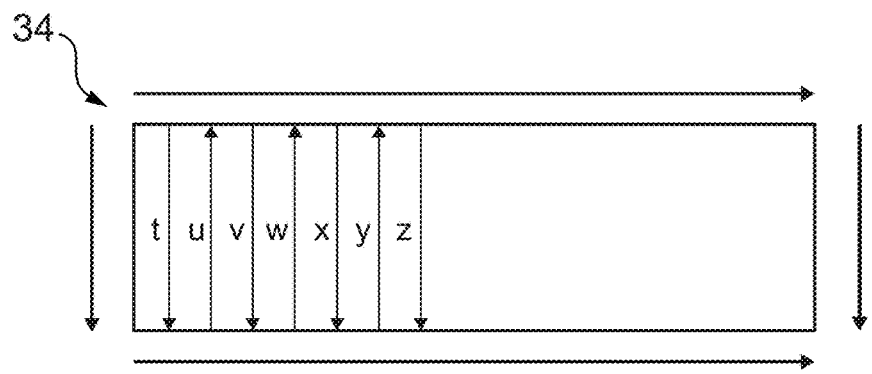
FIG. 10 is a schematic illustration of a linear path of movement of a laser beam of the laser-based system of FIG. 9.
Figure 11:
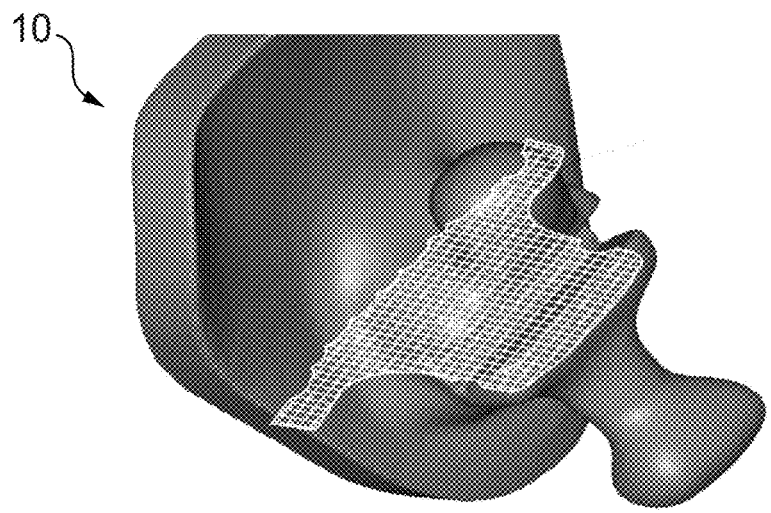
FIG. 11 is a schematic illustration of a linear path of movement of a laser beam of the laser-based system of FIG. 9.

In certain embodiments, the processor 350 of the laser-based system 120 is arranged to move the laser beam 210 stochastically (or randomly) to fuse the powder 220 (FIG. 10), which may help to reduce the internal stresses in the finished product. An example stochastic movement of the laser beam is shown in FIG. 9 in which the laser beam 210 travels in series along the paths a, b, c, d, e, f, g. In certain embodiments, the processor 350 of the laser-based system 120 is arranged to move the laser beam 210 along a linear path, as shown for example in FIGS. 10 and 11 as the paths t, u, v, w, x, y, z. In certain embodiments, the processor 350 of the laser-based system 120 is arranged to move the laser beam 210 in a combination of stochastic movement and linear movement.

The laser-based system 120 is arranged to build the bracket 10 layer-by-layer. In certain embodiments, the bracket 10 is built from the rear portion 17 towards the front portion 19, more specifically starting from the rear surface 26 of the tooth bonding pad 24 and building up the bracket, layer by layer to the body 20.

In this respect, according to certain embodiments of the present technology, the laser-based system 120 is arranged to manufacture at least one support 360 in the fusing portion 240 for supporting the bracket 10 whilst manufacturing the bracket 10 and for positioning the bracket 10 relative to the laser-beam path (best seen in FIG. 9). Whilst making the bracket 10 using the laser-based system 120, it should be noted that the angle of the laser beam 210 incident on the powder 220 on the manufacturing stand 310 in the fusing portion 240 is not always at 90 degrees, in certain embodiments. It should also be noted that according to certain embodiments of the present technology, different brackets 10 being manufactured by the laser-based system 120 have different supports 360 holding them at different angles and positions relative to the laser beam. After the bracket 10 is manufactured, the support 360 is arranged to be removed from the bracket 10.

Figure 12:
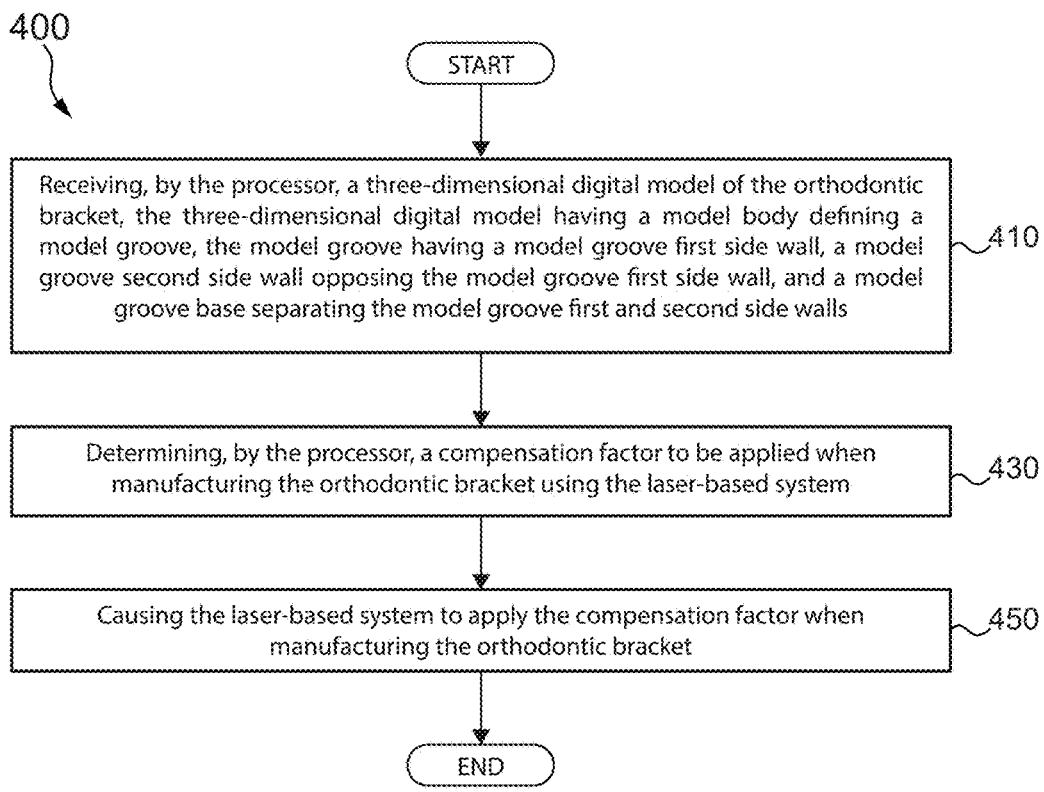
FIG. 12 is a schematic illustration of method steps in the manufacturing of an orthodontic bracket according to certain embodiments of the present technology.

With reference now to FIG. 12, in certain embodiments the computer system 110 is configured to execute the method 400 for making the orthodontic appliance, namely the orthodontic bracket 10. The method 400 will now be described in further detail below.

Step 410: Receiving, by the Processor, a Three-Dimensional Digital Model of the Orthodontic Bracket.

Figure 13:
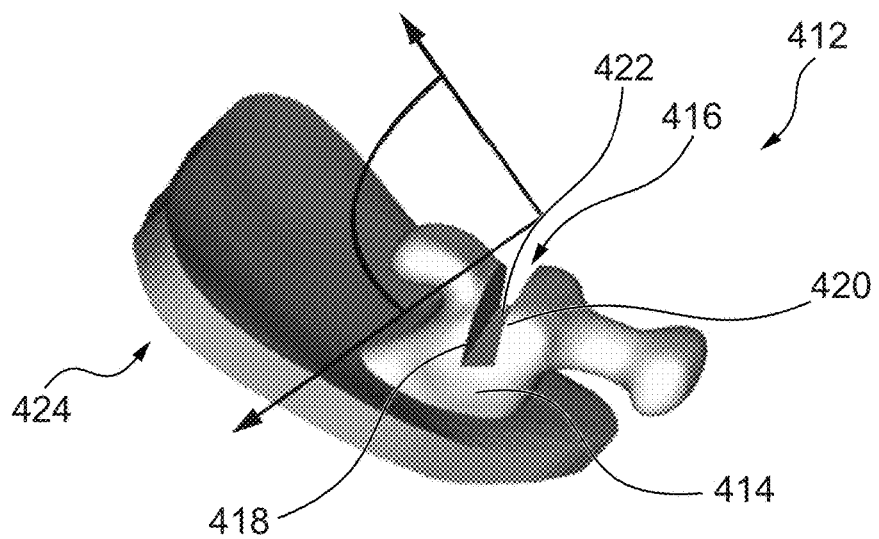
FIG. 13 is a perspective view of a three-dimensional digital model of the orthodontic bracket according to certain embodiments of the present technology.

The method commences with step 410 of the processor 150 receiving a three-dimensional digital model 412 of the orthodontic bracket 10 (FIG. 13). This three-dimensional digital model 412 will form at least a part of the basis of the instructions to the laser-based system 120 from the processor 150 for manufacturing the orthodontic bracket 10.

The three-dimensional digital model 412 of the orthodontic bracket 10 has a model body 414 defining a model groove 416, the model groove 416 having a model groove first side wall 418, a model groove second side wall 420 opposing the model groove first side wall 418, and a model groove base 422 separating the first and second groove model side walls 418, 420. The three-dimensional digital model of the orthodontic bracket 10 also has a model rear surface 424.

The three-dimensional digital model 412 includes an indication of a target manufactured dimension of certain parts of the orthodontic bracket. In certain embodiments, the three-dimensional digital model 412 includes information on a target manufactured dimension of the groove 22 of the orthodontic bracket 10 to be manufactured. The information on the target manufactured dimension of the groove 22 can include information on a length and a width of the groove, an angle between one or both of the groove side walls 30, 32 and the groove base 34, and an angle between the groove side walls 30, 32.

The three-dimensional digital model 412 can be embodied in any appropriate type and format, such as polygon mesh type. In certain embodiments, the three-dimensional digital model 412 is based on tooth data, such as from an intra-oral scanner or a CT scan of the tooth. Data on the contour of a surface of the tooth 16 from the tooth data can be used to define the contour of the model rear surface 424. Closely matching contours between the rear surface 26 of the bracket 10 and the tooth to which it is being applied can help with adhesion of the bracket to the tooth and comfort to the patient.

In certain embodiments, the method 400 further comprises obtaining tooth data on the tooth 16 of the patient, and generating the three-dimensional digital model 412 of the orthodontic bracket 10 using at least a portion of the tooth data. The tooth data may comprise image data of a crown portion of the tooth 16.

In certain embodiments, the receiving, by the processor 150, the three-dimensional digital model 412 of the orthodontic bracket 10 comprises importing the three-dimensional digital model 412 into a three-dimensional space. The processor 150 is then arranged to determine where to position the support 360 for that given bracket 10.

In this respect, in certain embodiments, the critical zone of the orthodontic bracket 10 is identified, the critical zone being at least one portion of the orthodontic bracket 10 which should not come into contact with the support 360 during manufacturing of the bracket 10. In certain embodiments, the critical zone is a predetermined location on the three-dimensional digital model 412. In certain embodiments, the critical zone is one or more of the model groove 416 and the model rear surface 424. The critical zone in the three-dimensional digital model 412 can be identified by an image recognition software.

In certain embodiments, the three-dimensional digital model 412 includes information regarding the critical zone for the given orthodontic bracket 10.

Once, the critical zone is identified, the processor 150 positions the at least one support 360 on the three-dimensional digital model 412, at a support position which is not the critical zone. The processor 150 re-orients the three-dimensional digital model 412 in the three-dimensional space to accommodate the support 360. In certain embodiments, the re-orienting can be performed manually.

Step 430: Determining, by the Processor, a Compensation Factor to be Applied when Manufacturing the Orthodontic Bracket Using the Laser-Based System.

The method 400 continues with Step 430 in which the processor 150 determines a compensation factor to be applied when manufacturing the orthodontic bracket using the laser-based system 120.

In certain embodiments, the compensation factor is instrumental in causing the groove, once manufactured, to meet a target manufactured dimension of the groove. The target manufactured dimension of the groove can be one or more of: a substantially 90 degree angle between one of the groove side walls 30 and the groove base 34, a substantially 90 degree angle between the other groove side wall 32 and the groove base 34, and the groove side walls 30, 32 being substantially parallel.

In certain other embodiments, the compensation factor is instrumental in causing the rear surface 26 to meet a target manufactured dimension or effect, such as a rear surface 26 texture or the label 36 on the rear surface 26. Similarly, the compensation factor can be used to ensure meeting target manufactured dimensions of any parts of the orthodontic device, such as the wings 28, the tooth bonding pad 24, etc.

In a broad sense, the compensation factor relates to a deviation of a position of the model groove base 422 from a desired position of the model groove base 422 when the three-dimensional digital model 412 of the orthodontic bracket 10 has been re-oriented to include the support 360.

In certain embodiments, the re-orienting results in the model body 414 being positioned such that a plane of the model groove base 422 is at an angle relative to the laser beam 210 of less than or more than 90 degrees.

Figure 14:
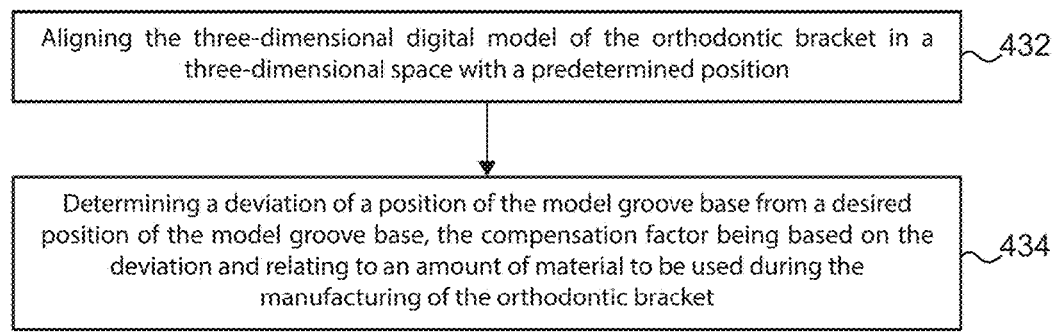
FIG. 14 is a schematic illustration of method steps in the manufacturing of an orthodontic bracket according to certain embodiments of the present technology.

More specifically, the determination of the compensation factor is determined according to Steps 432 and 434 (FIG. 14). In Step 432, the method 400 comprises aligning the three-dimensional digital model 412 of the orthodontic bracket 10 in the three-dimensional space with a predetermined position of the three-dimensional model 412. This is a pre-cursor step to determining a deviation of the model groove base 422 plane from a desired position of the model groove base 422. In Step 434, the method 400 comprises determining the deviation of the position of the model groove base 422 from the desired position of the model groove base 422, the compensation factor being based on the deviation.

The compensation factor can be considered as a compensation of larger than normal manufacturing tolerances when the laser-based system 120 is making certain parts of the bracket 10, which tolerances may be related to an angle of incidence of the laser beam 210 with certain parts of the bracket 10 during its manufacture. In certain embodiments, the compensation factor relates to an amount of material to be used during the manufacturing of the orthodontic bracket 10. By material is meant the metal particles 220, for example.

The amount of material to be used can be the amount of the material to be used to define the groove base 34. For example, referring to the laser-based system of FIG. 8, the amount of material can be the amount of the particles 220 supplied to the fusing portion 240 of the laser-based system 120 which are subsequently sintered to form the groove base 34. Alternatively, or in addition, the amount of material to be used during the manufacturing of the orthodontic bracket 10 can be the amount of the particles 220 to be contacted by the laser beam 210. In this respect, the amount of material can also refer to a parameter of the laser beam 210, such as one or more of a spot diameter of the laser beam 210, a movement of the laser beam 210, and an area covered by the laser beam 210.

The amount of material used will define the groove base 34 in terms of dimensions of the groove 22, such as one or more of: a depth of the groove 22, a height of the side walls 30, 32, a width of the side walls 30, 32, a width of the groove base 34, and a length of the groove base 34.

In certain embodiments, the amount of material is for reducing the material applied when defining the groove base 34. For example, the method 400 can be used to optimize the amount of material used in forming the groove base 34 in order to achieve a groove 22 with target manufactured dimension. This could also be achieved by adapting the laser beam path. By optimizing the amount of material can mean, in certain embodiments, reducing the amount of material used to manufacture the bracket whilst obtaining the target manufactured dimension.

Figure 15:
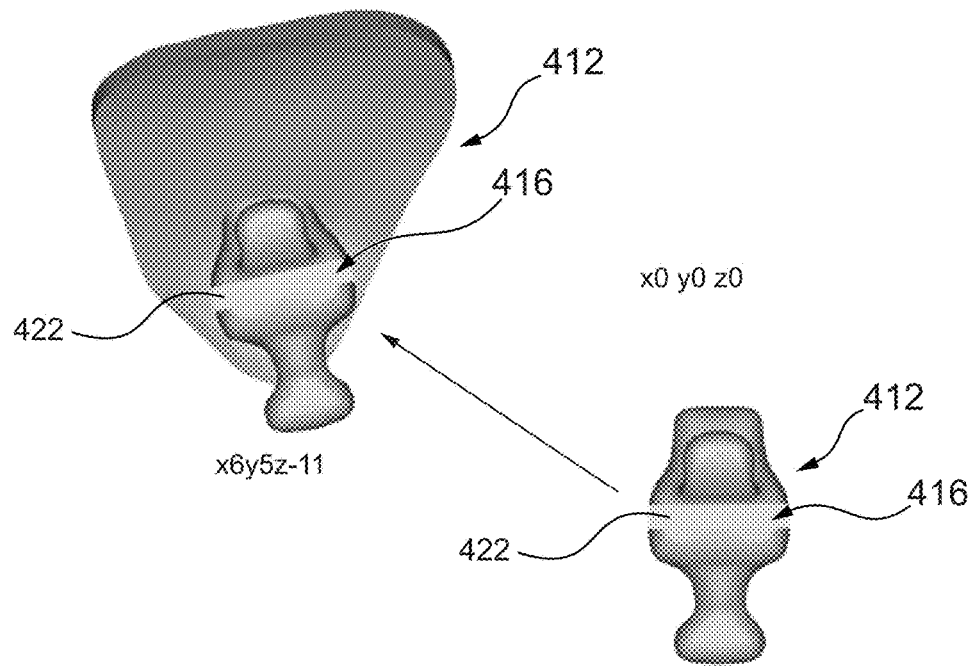
FIG. 15 is a schematic illustration of the three-dimensional digital model of FIG. 12, with portions removed for clarity, and illustrating a start position and a predetermined position, according to certain embodiments of the present technology.

Referring now to the alignment of the three-dimensional digital model 412 with the predetermined position in Step 432, the position of any part of the three-dimensional digital model 412 can be identified as an x, y, z coordinate in space, or an x, y coordinate in space. When the three-dimensional digital model 412 is received in Step 410 by the processor 150, it is imported into a starting position, shown as x0y0z0 in FIG. 15. Alignment of the three-dimensional digital model 412, if it is not already aligned with the predetermined position, comprises moving the three-dimensional digital model 412 to the predetermined position, shown as x6y5z–11 in FIG. 15.

In certain embodiments, the predetermined position of the three-dimensional digital model 412 of the orthodontic bracket 10 comprises a predetermined x, y position of the model groove base 422 of the three-dimensional digital model 412.

Accordingly, the method 400 further comprises, in certain embodiments, determining if the model groove base 422 is aligned with the predetermined x, y position, and if the model groove base 422 is not aligned with the predetermined x, y position, causing the three-dimensional digital model 412 of the orthodontic bracket 10 to move in the three-dimensional space to the predetermined x, y position. The same pre-determined x, y position may be used for different orthodontic brackets 10 of a set of orthodontic brackets (e.g. for the upper jaw and/or the lower jaw).

Developers have identified that the z direction alignment of the three-dimensional digital model 412 is not always required. Therefore, in certain embodiments, the predetermined position of the three-dimensional digital model 412 of the orthodontic bracket 10 does not include taking into account a z-direction position of the model groove base 422 of the three-dimensional digital model 412.

Figure 16:
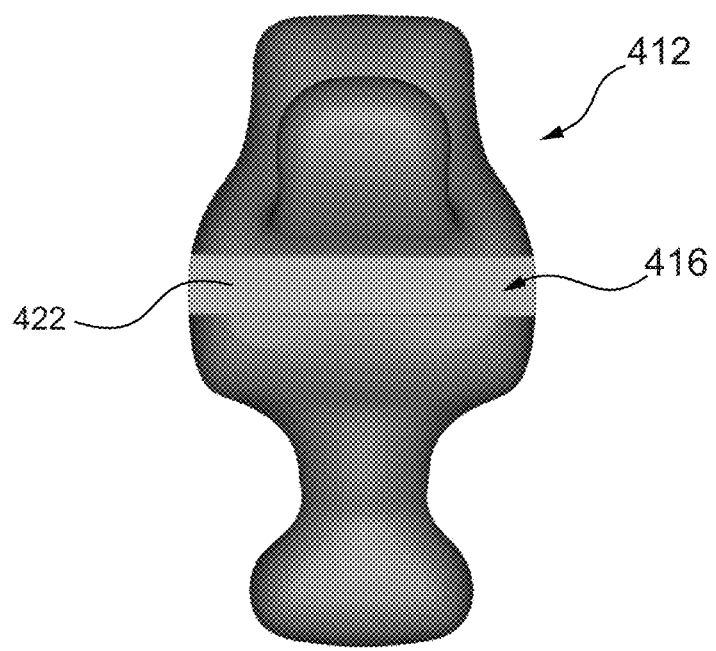
FIG. 16 is a top-plan view of the three-dimensional digital model of FIG. 12, with portions removed for clarity, and highlighting a model groove base, according to certain embodiments of the present technology.

Before determining if the model groove base 422 is aligned with the predetermined position, the method 400 comprises identifying the model groove 416 from the three-dimensional digital model 412 (shown as highlighted rectangle in FIG. 16). Image processing software and methods, for example, can be used to detect the model groove base 422, such as by delineating the borders of the model groove base 422 from the surrounding features of the three-dimensional digital model 412.

If it is determined that the model groove base 422 is not aligned with the predetermined x, y position, the method 400 comprises causing the three-dimensional digital model 412 of the orthodontic bracket 10 to move in the three-dimensional space to the predetermined x, y position.

Figure 17A:
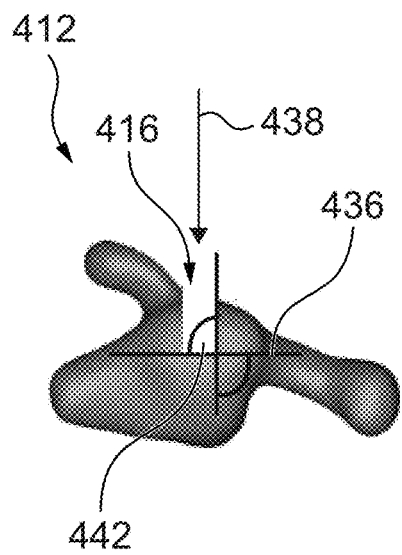
FIGS. 17A and 17B is a side view and an end view respectively, of the three-dimensional digital model of FIG. 12, with portions removed for clarity, according to certain embodiments of the present technology.
Figure 17B:
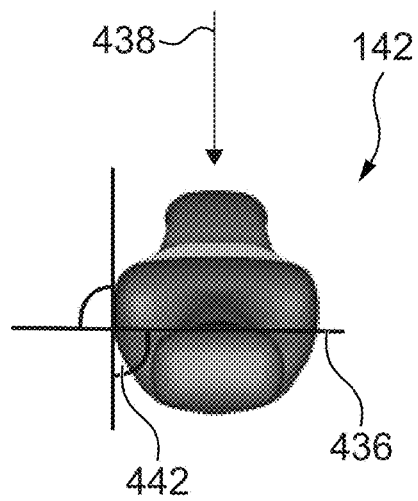

Referring now to determining the deviation of the position of the model groove base 422 from a desired position of the model groove base 422 in Step 434, reference is made to FIGS. 17A and 17B showing a side view and an end view, respectively, of the three-dimensional digital model 412 in the predetermined x, y position.

In certain embodiments, the desired position is a position relative to a path 438 of the laser beam 210 of the laser-based system 120. In certain embodiments, the desired position is a reference plane 436 substantially perpendicular to the path 438 of the laser beam 210 of the laser-based system 120. In certain embodiments, the position of the model groove base 422 is a plane 440 of the model groove base 422.

Figure 18:
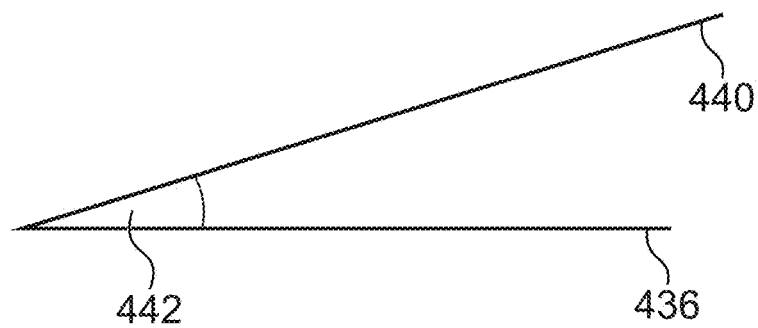
FIG. 18 is an illustration of the model groove base of a three-dimensional digital model of FIG. 12 and a reference plane, according to certain embodiments of the present technology.

The compensation factor is based on an angle of deviation 442 between the plane of the model groove base 422 and the reference plane 436 (FIG. 18). The angle of deviation can be obtained in one or more of the x axis, and the y axis. In certain other embodiments, the desired position of the model groove base 422, can be any other reference position.

The compensation factor is determined based on the deviation between the model groove base 422 and the desired position of the model groove base 422. In certain embodiments, this determination is based on a pre-determined table of compensation factors, and example of which is shown in table 1 below. The compensation factors of Table 1 were compiled by the Developers of the present technology based on exhaustive tests and experiments.

TABLE 1

| One embodiment of a pre-determined table of compensation factors | |
| --- | --- |
| Deviation between the model groove base and the desired position of the model groove base | Compensation factor |
| x-axis (0-10) degrees y-axis (0-10) degrees | Groove increase of 0.01 mm |

TABLE 1-continued

| One embodiment of a pre-determined table of compensation factors | |
| --- | --- |
| Deviation between the model groove base and the desired position of the model groove base | Compensation factor |
| x-axis (10-90) degrees y-axis (10-90) degrees | Groove increase of 0.02 mm |
| x-axis (0-10) degrees x-axis (0-10) degrees OR x-axis (10-90) degrees y-axis (0-10) degrees | Groove increase of 0.015 mm |

In the embodiment illustrated in table 1, for a deviation of 0-10° on the x or the y axis of the model groove base 422 from the desired position of the model groove base 422, the compensation factor is based on a required groove increase of 0.01 mm. Accordingly, the material to be used to define the groove base 34 is reduced by an appropriate amount.

For a deviation of 10-90° on the x or the y axis of the model groove base 422 from the desired position of the model groove base 422, the compensation factor is based on a required groove increase of 0.02 mm. Accordingly, the material to be used to define the groove base 34 is reduced by an appropriate amount.

For a deviation of 0-10° on one of the x or the y axis, and 10-90° on the other of the x or the y axis, the compensation factor is based on a required groove increase of 0.015 mm. Accordingly, the material to be used to define the groove base 34 is reduced by an appropriate amount.

Step 450: Causing the Laser-Based System to Apply the Compensation Factor for Manufacturing the Orthodontic Bracket.

In Step 450, the laser-based system 120 is caused to apply the compensation factor for manufacturing the orthodontic bracket 10. In this regard, in certain embodiments, the method comprises modifying or adapting the three-dimensional digital model 412 according to the compensation factor, before sending instructions for the manufacturing of the bracket 10 to the laser-based system 120 based on the compensated three-dimensional digital model 412. This can involve adapting the dimensions of the model groove 416 according to the determined compensation factor. According to the examples shown in Table 1, the dimensions of the model groove 416 would be increased by the identified amounts in one or more of the x, y and z directions. In other words, the groove size would be increased which would translate to less material being required during the manufacture of the bracket 10.

In certain embodiments, the method 400 further comprises a step of sending instructions to the laser-based system for manufacturing the orthodontic bracket 10 according to the compensated three-dimensional digital model 412. Accordingly, the compensated three-dimensional digital model 412 is processed into slices before sending to the laser-based system 120 in a suitable format (e.g. SLC format). The instructions may include instructions regarding the support 360 including its position and configuration.

Figures 19, 20:
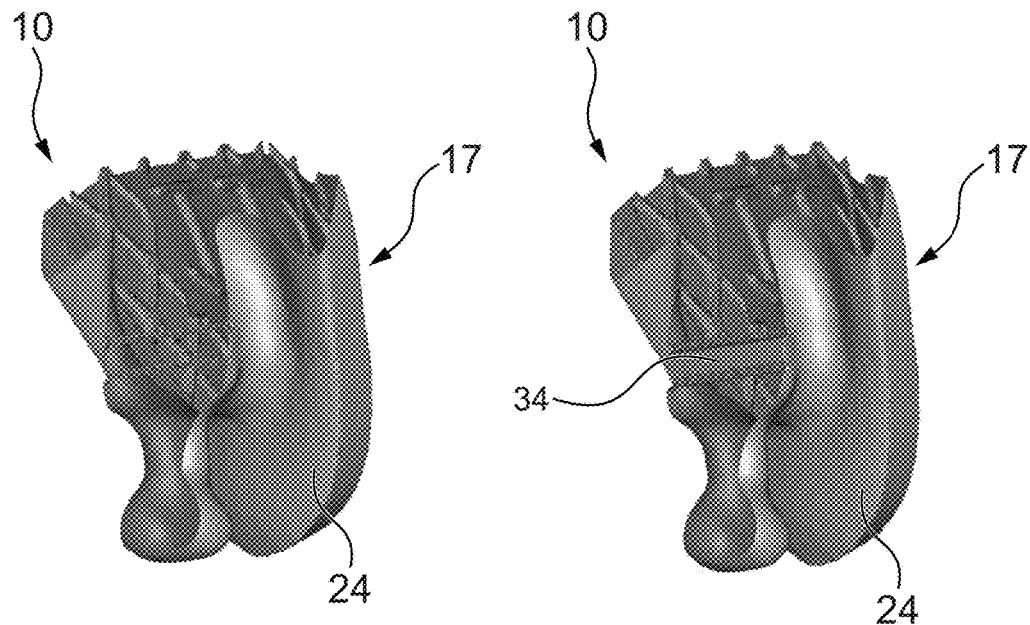
FIG. 19 illustrates a partially manufactured orthodontic bracket in which a groove base has not yet been formed, according to certain embodiments of the present technology.
FIG. 20 illustrates a partially manufactured orthodontic bracket in which a groove base has been formed, according to certain embodiments of the present technology.

The instructions may include instructing the formation of the base 34 of the groove 22 in a single operation (FIGS. 19 and 20). In other words, a surface layer of the base 34 of the groove 22 is formed separately than the surrounding layer on the same plane within the bracket 10. An edge portion of the groove 22 is formed initially (FIG. 19) followed by the base 34 of the groove 22. In these embodiments, the groove 22 is formed through a stochastic movement of the laser beam 210 incident on the groove, such as illustrated in FIG. 9. In certain embodiments, a surface layer of the base 34 of the groove 22 is formed together with the surrounding layer on the same plane in a stochastic manner.

During the additive manufacturing of the bracket 10 according to embodiments of the present technology, the bracket 10 may be supported such that the rear surface 26 of the bracket 10 being built has a substantially 45° angle with the support 360.

It should be expressly understood that not all technical effects mentioned herein need to be enjoyed in each and every embodiment of the present technology.

Modifications and improvements to the above-described implementations of the present technology may become apparent to those skilled in the art. For example, the present technology may also be applied to the manufacture of orthodontic appliances other than orthodontic brackets. The foregoing description is intended to be exemplary rather than limiting. The scope of the present technology is therefore intended to be limited solely by the scope of the appended claims.

The invention claimed is:

1. A method for making an orthodontic appliance having a body defining a groove, the groove having a first groove side wall, a second groove side wall opposing the first groove side wall, and a groove base separating the first and second groove side walls, the method executable by a processor of a computer system operatively connected to a laser-based system, the method comprising:
    receiving, by the processor, a three-dimensional digital model of the orthodontic appliance, the three-dimensional digital model having a model body defining a model groove, the model groove having a model groove first side wall, a model groove second side wall opposing the model groove first side wall, and a model groove base separating the first and second groove model side walls;
    determining, by the processor, a compensation factor to be applied when manufacturing the orthodontic appliance using the laser-based system, the determining the compensation factor including:
        aligning the three-dimensional digital model of the orthodontic appliance in a three-dimensional space with a predetermined position;
        determining a deviation of a position of the model groove base from a desired position of the model groove base, the compensation factor being based on the deviation and relating to an amount of material to be used during the manufacturing of the orthodontic appliance;
    causing the laser-based system to apply the compensation factor for manufacturing the orthodontic appliance.

2. The method of claim 1, wherein the amount of material to be used is the amount of the material to be used to define the groove base.

3. The method of claim 1, wherein the amount of material is for reducing the material applied when defining the groove base.

4. The method of claim 1, wherein the desired position is a reference plane substantially perpendicular to the path of the laser beam of the laser-based system, and the position of the model groove base is a plane of the model groove base.

5. The method of claim 4, wherein the compensation factor is based on an angle of deviation between the plane of the model groove base and the reference plane.

6. The method of claim 1, wherein determining the compensation factor comprises accessing a pre-determined table of compensation factors.

7. The method of claim 1, wherein the three-dimensional digital model further includes an indication of a target manufactured dimension of the groove, and wherein the compensation factor is instrumental in causing the groove, once manufactured, to meet the target manufactured dimension of the groove.

8. The method of claim 7, wherein the target manufactured dimension of the groove is one or more of:
    a substantially 90 degree angle between the first groove side wall and the groove base;
    a substantially 90 degree angle between the second groove side wall and the groove base; and
    the first groove side wall and the second groove side wall being substantially parallel.

9. The method of claim 1, wherein the predetermined position of the three-dimensional digital model of the orthodontic appliance comprises a predetermined x, y position of the model groove base of the three-dimensional model.

10. The method of claim 1, wherein the predetermined position of the three-dimensional digital model of the orthodontic appliance does not include taking into account a z-direction position of the model groove base of the three-dimensional digital model.

11. The method of claim 9, wherein the aligning the three-dimensional digital model comprises identifying the model groove from the three-dimensional digital model, determining if the model groove base is aligned with the predetermined x, y position, and if the model groove base is not aligned with the predetermined x, y position, causing the three-dimensional digital model of the orthodontic appliance to move in the three-dimensional space to the predetermined x, y position.

12. The method of claim 1, further comprising causing the laser-based system to manufacture at least one of (i) the groove base of the orthodontic appliance, and (ii) the orthodontic appliance in a single operation.

13. The method of claim 1, further comprising causing the laser beam to move stochastically.

14. The method of claim 1, wherein the laser-based system is a selective laser sinter system.

15. The method of claim 1, further comprising obtaining tooth data on a tooth of a patient, and generating the three-dimensional digital model of the orthodontic appliance using at least a portion of the tooth data.

16. A system for making an orthodontic appliance having a body defining a groove, the groove having a first groove side wall, a second groove side wall opposing the first groove side wall, and a groove base separating the first and second groove side walls, the system comprising:
    a computer system, operatively connected to a laser-based system, and having a processor arranged to determine a compensation factor to be applied when manufacturing the orthodontic appliance using the laser-based system; and
    a laser-based system for manufacturing the orthodontic appliance based on instructions from the processor of the computer system, including the compensation factor,
    the processor being arranged to:
        receive a three-dimensional digital model of the orthodontic appliance, the three-dimensional digital model having a model body defining a model groove, the model groove having a model groove first side wall, a model groove second side wall opposing the model groove first side wall, and a model groove base separating the first and second groove model side walls;

determine the compensation factor by:
aligning the three-dimensional digital model of the orthodontic appliance in a three-dimensional space with a predetermined position; and determining a deviation of a position of the model groove base from a desired position of the model groove base, the compensation factor being based on the deviation and relating to an amount of material to be used during the manufacturing of the orthodontic appliance.

17. A method for making an orthodontic appliance having a first portion defining a groove, and a second portion having a rear surface, the method executable by a processor of a computer system operatively connected to a laser-based system, the method comprising:

receiving, by the processor, a three-dimensional digital model of the orthodontic appliance;

determining, by the processor, a compensation factor to be applied to the movement of a laser beam of the laser-based system when manufacturing at least one of the first portion or the second portion of the appliance, wherein the compensation factor relates to an amount of material to be used during the manufacturing of the orthodontic appliance when manufacturing at least one of the first portion or the second portion of the appliance at an angle relative to the incident laser beam which is not an optimized angle for laser-based manufacturing; and causing the laser-based system to manufacture the orthodontic appliance based on the three-dimensional digital model and the compensation factor during manufacturing of at least one of the first portion or the second portion of the orthodontic appliance.

18. The method of claim 17, wherein the determining the compensation factor comprises:

aligning the three-dimensional digital model of the orthodontic appliance in a three-dimensional space with a predetermined position; and determining a deviation of a position of a model groove base of the three-dimensional digital model from a desired position of the model groove base, the compensation factor being based on the deviation of the position and relating to an amount of material to be used during the manufacturing of the orthodontic appliance.

* * * * *